United States Patent [19]

Sullivan

[11] 4,155,881

[45] May 22, 1979

[54] ACTIVATION OF CHROMIC FLUORIDE CATALYST WITH HYDROGEN CHLORIDE AND CHLORINE

[75] Inventor: Raymond Sullivan, Newark, Del.

[73] Assignee: E. I. Du Pont de Nemours and Company, Wilmington, Del.

[21] Appl. No.: 884,711

[22] Filed: Mar. 8, 1978

[51] Int. Cl.$^2$ .................. B01J 27/12; B01J 27/32; C07C 17/00; C07C 19/08

[52] U.S. Cl. .................. 252/441; 252/415; 260/653.7

[58] Field of Search .................. 252/415, 441; 260/653.7; 423/442

[56] References Cited

U.S. PATENT DOCUMENTS

| | | | |
|---|---|---|---|
| 2,977,323 | 3/1961 | Johnson et al. | 252/415 |
| 3,150,104 | 9/1964 | Lehman | 252/415 |
| 3,294,852 | 12/1966 | Vecchio | 260/653.7 |
| 3,385,794 | 5/1968 | Sherer et al. | 252/415 |
| 3,632,834 | 1/1972 | Christoph, Jr. | 260/653.7 |
| 3,660,307 | 5/1972 | Sherer et al. | 252/415 |
| 3,855,151 | 12/1974 | Shindel | 252/415 |

Primary Examiner—Patrick Garvin
Assistant Examiner—P. E. Konopka
Attorney, Agent, or Firm—James A. Costello

[57] ABSTRACT

A process for activating chromic fluoride halogen-exchange catalyst, comprising contacting the catalyst with hydrogen chloride and then chlorine, or, hydrogen chloride and chlorine, simultaneously, and contacting the intermediate chloride-containing compound thus formed with hydrogen fluoride to complete the activation.

11 Claims, No Drawings

ACTIVATION OF CHROMIC FLUORIDE CATALYST WITH HYDROGEN CHLORIDE AND CHLORINE

BACKGROUND OF THE INVENTION

The chromic fluoride catalysts activated by the process of this invention are useful in vapor phase halogen-exchange reactions between hydrogen fluoride and one and two carbon chlorocarbon compounds. The fluorocarbon compounds and chlorofluorocarbon compounds formed by said halogen-exchange reactions are useful, among other things, as refrigerants, aerosol propellants, solvents, and dielectric gases.

Chromic fluoride catalysts are normally packed in heated fixed-bed tower reactors through which the reactants are passed in the gas phase. In this use, the so-called activity of the catalyst, as measured by the degree of exchange of fluorine for chlorine per pass, gradually decreases until it is no longer economical to operate the column and the (spent) catalyst must be replaced. Typically, such reactors can be operated for about 750 to 1,500 hours before the catalyst must be replaced. Replacement of catalyst is expensive in terms of materials cost and lost production time.

Coassigned U.S. Pat. No. 3,855,151, discloses a method for reactivating spent chromic fluoride catalysts which comprises reacting said catalysts with a chlorine-source such as a $C_1$ or $C_2$ chlorocarbon capable of dissociating at reaction temperatures of 300° to 500° C. to produce chlorine, or, with a combination of chlorine plus a $C_1$ or $C_2$ chlorocarbon not capable of dissociation at such reaction temperatures. Said patent does not concern the $HCl/Cl_2$ reaction of this invention. Art references relating to the regeneration of cracking catalysts or chromium oxyfluoride catalysts are not pertinent to the process of this invention because of the significantly different chemistry there involved.

The process of this invention has certain very desirable characteristics. For example, organic materials which are foreign to the compounds being made are not introduced by the instant process. The process is operable at atmospheric pressure but is more preferably operated at superatmospheric pressures. Operation at superatmospheric pressures makes it unnecessary to store or discard the process charge at the beginning of activation in order to return to atmospheric pressure. Instead, the charge is merely displaced through the normal recovery train by the activating chemicals. Finally, the catalyst activated according to the process of this invention has a relatively long useful life and its activity is better than would be expected by one skilled in the art.

SUMMARY OF THE INVENTION

This invention concerns a process for activating chromic fluoride halogen-exchange catalyst, said process comprising the steps of contacting said catalyst with hydrogen chloride (HCl) and then chlorine ($Cl_2$), or, with hydrogen chloride and chlorine, simultaneously, for a time sufficient to convert at least a part of said chromic fluoride to chromic chloride.

The compound formed by contacting the catalyst with hydrogen chloride and chlorine, in the manner described above, when placed in service in a halogen-exchange reaction, is converted to chromic fluoride by the hydrogen fluoride (HF) reactant. It is preferred, however, to contact said chromic chloridecontaining compound with HF before it is placed in service (whether for its first use or for any subsequent reuse).

The process of this invention is useful to activate catalysts whose activities have been reduced in a halogen-exchange reaction as well as catalysts which have never been used in a halogen-exchange reaction. For instance, newly prepared catalysts can be beneficiated by the process of this invention to the extent that they do not display expected levels of activity. This invention is not limited to the activation of catalysts which display little or no activity. Rather, the process is operable to make active catalyst even more active. The term "catalyst" as employed herein refers to chromic fluoride before, during, and after activation. Catalyst beneficiated according to the process of this invention is referred to as "activated" where its activated condition is not clear from the context.

It will be appreciated by those skilled in the art that times, temperatures and pressures are interrelated and can be varied within the scope of this description to produce desired results. For instance, higher temperatures, with or without increased feed pressures, can be employed to decrease the reaction times required to achieve a desired level of activity. In the same way, pressures can be varied to affect reaction times, with or without attendant changes in temperature. Within the limits explained herein, reaction times can be varied in light of the particular temperatures and/or pressures which are employed.

DETAILS OF THE INVENTION

The catalyst activated by the process of this invention can be in bulk form or it can be supported, for example, on a carbon support. It is preferred to employ supported chromic fluoride for the halogen-exchange processes which are contemplated herein to use chromic fluoride catalyst activated by the process of this invention. For that reason, the process of this invention will be most likely to find utility in activating supported catalysts. It is preferred to employ the present process on supported chromic fluoride which is easier to work with than is bulk chromic fluoride.

The bulk form of the catalyst can be prepared by partial dehydration of a chromic chloride hydrate such as $CrCl_3.6H_2O$ to a lower hydrate followed by treatment with HF at elevated temperatures, e.g., greater than 200° C. (with about 400° C. being preferred), which first converts the $CrCl_3$ hydrate to the anhydrous form, then replaces chlorine with fluorine to form $CrF_3$.

The chromic fluoride-on-carbon catalysts can be prepared by treating the carbon support with an aqueous solution of chromic chloride hexahydrate ($CrCl_3.6H_2O$) until the desired amount of the chromium salt is absorbed. The solids are then dried to evaporate water, e.g., at about 110° C. The superficially dry solids are then further dried at 400° C. with gaseous hydrogen fluoride.

X-ray and electron diffraction studies of catalysts produced in this manner indicate the chromium to be in the form of chromic fluoride, free of detectable oxygen. If, instead of $CrCl_3.6H_2O$, one were to start with a hydrous chromic fluoride such as $CrF_3.3H_2O$ or $CrF_3.4H_2O$ in the preparation of catalyst, the resulting catalyst would contain predominantly a chromium oxyfluoride which is not useful in the halogenexchange reactions described herein.

Without wishing to be bound by any theory of how the invention works, it is believed that the activation of chromic fluoride catalyst may take place in the following steps:

(i) Metathesis occurs between HCl and the chromic fluoride to convert the chromic fluoride to chromic fluoride or mixed chromic chlorofluorides; the discovery of this metathetical reaction is one of the most important aspects of this invention; it is only by appreciation of the mechanics of this reaction that the discovery was made that HCl and $Cl_2$ must be introduced to the catalyst in the precise manner that has been described; contacting with chlorine first and then with HCl will not provide an operable process;

(ii) In the presence of chlorine, which may be provided simultaneously or in a separate following step, the chromic chloride or mixed chlorofluorides are rendered mobile and thus redistributed in small crystals of large surface area. Treatment with HF of the redistributed chromic chloride or mixed chlorofluorides reconverts them to catalytically active chromic fluoride.

HCl should be used in an amount sufficient to convert chromic fluoride to chromic chloride. Because the reaction is an equilibrium reaction favoring the chromic fluoride, it is necessary to use more than equivalent amounts of HCl. It has been found that HCl serves the additional functions of transferring heat and sweeping products from the catalyst. An excess of about 30 to 40 times the amount of HCl needed to convert all chromic fluoride to chromic chloride is preferred.

Enough chlorine is used to mobilize at least part of the chromic chloride. For example, about one half to three mole percent of chlorine in HCl is preferred with about 1.7 mole percent being most preferred. Smaller or larger amounts are also useful. During activation, it is preferred to provide about 37 parts by weight of the most preferred mixture of HCl and $Cl_2$ to the catalyst per part of chromic fluoride. For best results, using said mixture, about 20 hours of treatment time are employed at average reactor temperatures of about 425° C. to 450° C. Temperatures of 475° C. are operable and somewhat higher temperatures may also be used.

If chlorine is employed in sequence after hydrogen chloride, it should be used in an amount sufficient to mobilize at least part of the chromic chloride. The requisite amount of chlorine for that purpose can be readily determined by one skilled in the art on the basis of the description herein provided.

Atmospheric and superatmospheric pressures can be employed during the step of contacting the catalyst with hydrogen chloride and chlorine. It is preferred that superatmospheric pressures be used, preferred pressures being between about 17 to 25 kilograms per square centimeter (about 240 to 360 pounds per square inch).

HF is normally employed in at least an equivalent amount for conversion of chromic chloride to chromic fluoride. When the catalyst is reconverted to chromic fluoride, the concentration of HF is preferably increased slowly until it reaches about 50 weight percent (64.6 mole percent) in the HCl stream to avoid overheating. A treatment time, at about 200° to 400° C., of some 8 to 10 hours will complete catalyst activation.

EXAMPLES

In Examples 1 and 2, spent catalysts were charged to laboratory size packed reactor columns. Without removing the catalyst from the column, the catalyst was tested for activity, thereafter subjected to activating conditions, and then retested for activity.

The test for activity consisted in passing a mixture of 1,1,2-trichloro-1,2,2-trifluoroethane, sometimes containing 1,1,2,2-tetrachloro-1,2-difluoroethane to simulate a plant stream, and hydrogen fluoride over the catalyst and analyzing the effluent to determine the conversion to more highly fluorinated 1,2-dichloro-1,1,2,2-tetrafluoroethane.

The test reactor of Example 1 comprised a column simulating a commercial reactor tower, made from two vertical pieces of 2.54×76.2 cm nickel-chromium ("Inconel") pipe connected at the bottom to describe a U-shaped reactor and packed with 454 grams of 20 weight percent of $CrF_3$-on-carbon catalyst. The catalyst employed had become spent in the catalysis of halogen exchange between hydrogen fluoride and hexachloroethane, the latter having been prepared in situ by feeding tetrachloroethylene and an equivalent amount of chlorine. The reactor was immersed in a molten bath of a eutectic mixture of $KNO_3$, $NaNO_3$ and $NaNO_2$ ("Hitec"). An electrical preheater was employed to bring the temperature of the entering gases to the temperature of the molten bath.

When the device was employed in the test for catalyst activity, a mixture of hydrogen fluoride and 1,1,2-trichloro-1,2,2-trifluoroethane (and in some cases small amounts of 1,1,2,2-tetrachloro-1,2-difluoroethane) was fed to the upstream leg. Gases passing out of the reactor were passed through an ice-chilled 5 weight percent aqueous KOH bubbler, where a part of the organic product condensed and the hydrogen fluoride was neutralized. The gas stream leaving the bubbler was passed through a gas sampling bulb to a gas volume measuring device. The collected liquid sample and the gas sample were analyzed by gas chromatography. From the data of the experiment, the amount of 1,2-dichloro-1,1,2,2-tetrafluoroethane formed was calculated. This number, in moles, divided by the number of moles of organic feed charged and the result multiplied by 100 yielded the percent conversion which was taken as a measure of the activity of the catalyst.

When the device was used for the activation of catalyst, metered streams of hydrogen chloride under autogenous pressure and liquid chlorine under nitrogen pressure were charged to the preheater. The products leaving the reactor were discarded except as noted.

Activation experiments carried out at increasing temperatures using mixed hydrogen chloride and chlorine demonstrated that minimum operable temperatures can be determined easily for each catalyst batch. For best results, a temperature of at least about 425° C. is recommended. Except as noted, a control test preceded each activation to establish the activity of the spent catalyst. In the Procedures and Examples which follow, the expression "moles" is used to indicate the amounts of gram-moles employed.

Procedure 1

This procedure shows the attempted activation of spent 20 weight percent $CrF_3$-on-carbon catalyst at a temperature of 375° C. Although activation was unsuccessful in the time employed, 20 hours, one skilled in the art could easily determine whether activation at said temperature is possible if longer times are employed. In any event, such long-term activation procedures would not be preferred.

(a) Control Test (Untreated Spent Catalyst)

At a pressure of 270 psig (19.0 kg cm$^{-2}$) and a molten salt bath temperature of 310° C., a stream consisting of:
  HF (11.3 moles hr$^{-1}$);
  1,1,2-trichloro-1,2,2-trifluoroethane (5.5 moles hr$^{-1}$); and
  1,1,2,2-tetrachloro-1,2-difluoroethane (1.7 moles hr$^{-1}$)
was passed through the catalyst. Of the organic feed, 0.2 to 0.4 mole percent was found to have been converted to 1,2-dichloro-1,1,2,2-tetrafluoroethane at steady state.

(b) Activation

At a pressure of 270 psig (19.0 kg cm$^{-2}$) and molten salt bath temperature of 375° C., a stream consisting of:
  HCl (4.9 moles hr$^{-1}$); and
  Cl$_2$ (0.059 mole hr$^{-1}$, 1.19 mole percent)
was passed through the catalyst for 20 hours. Thereafter, the salt bath was allowed to cool under HCl flow to 310° C. during 12 hours.

(c) Conversion Activity Test

There was no increase in conversion to 1,2-dichloro-1,1,2,2-tetrafluoroethane over that observed in the control test under the same conditions.

Procedure 2

Activation was attempted at 400° C. for 20 hours.

(a) Control Test

At a pressure of 270 to 280 psig (19.0 to 19.7 kg cm$^{-2}$) and molten salt bath temperature of 360° C., a stream consisting of:
  HF (11.3 moles hr$^{-1}$); and
  1,1,2-trichloro-1,2,2-trifluoroethane (3.6 moles hr$^{-1}$)
was passed through a fresh charge of spent catalyst until the composition of the effluent was constant. Of the organic feed, 2.8 mole percent was found to have been converted to 1,2-dichloro-1,1,2,2-tetrafluoroethane.

(b) Activation

The activation of Procedure 1 was repeated with the exception that the molten salt temperature was 400° C. and the salt bath was allowed to cool under HCl flow to 310° during 10 hours.

(c) Conversion Activity Test

At a pressure of 270 psig (19.0 kg cm$^{-2}$) and a salt bath temperature, raised during 51 hours, from 310° C. to 360° a stream consisting of:
  HF (11.3 moles hr$^{-1}$);
  1,1,2,-trichloro-1,2,2-trifluoroethane (2.72 moles hr$^{-1}$); and
  1,1,2,2-tetrachloro-1,2-difluoroethane (0.83 moles hr$^{-1}$)
was passed through the catalyst. Analysis of the effluent showed that, of the organic feed, 0.2 mole percent was converted to 1,2-dichloro-1,1,2,2-tetrafluoroethane at 310° C., 1.5 mole percent was converted at 340° C., and about 5 mole percent at 360° C.

EXAMPLE 1

(a) Control Test

The catalyst was of the same lot as that of Procedure 2.

(b) Activation

At a pressure of 270 psig (19.0 kg cm$^{-2}$) and molten salt bath temperature of 425° C., a stream consisting of:
  HCl (4.9 moles hr$^{-1}$); and
  Cl$_2$ (0.088 mole hr$^{-1}$, 1.76 mole percent) was passed through the catalyst for 20 hours.

Analysis of the KOH scrubber contents, through which the effluent of this activation was brought, showed that 42 g of F$^-$, in the form of HF, was displaced from the catalyst. Theoretical F$^-$ on the catalyst in the form of CrF$_3$ was 47 g.

The reactor was allowed to cool to 310° C. during 4½ hours under HCl flow. In this experiment, fluorine substitution was carried out separately in advance of the conversion activity test by passing HF through the catalyst for 4 hours.

(c) Conversion Activity Test

At a pressure of 270 psig (19.0 kg cm$^{-2}$) and a salt bath temperature of 310° to 340°, a stream consisting of:
  HF (11.3 moles hr$^{-1}$);
  1,1,2-trichloro-1,2,2-trifluoroethane (2.72 moles hr$^{-1}$); and
  1,1,2,2-tetrachloro-1,2-difluoroethane (0.83 moles hr$^{-1}$)
was passed through the catalyst. Analysis of the effluent at a molten salt bath temperature of 340° C. showed that, of the organic feed, 22.9 mole percent was converted to 1,2-dichloro-1,1,2,2-tetrafluoroethane. In commercial practice, the temperature would be raised to and above 340° C. only after the activity of the catalyst had degraded. Observed conversions at lower temperatures were at 310° C., 0.75 mole percent and at 330° C., 6.2 mole percent.

EXAMPLE 2

This Example was carried out in a U-shaped reactor of the same size as that employed in Example 1. Atmospheric pressure was employed. An amount of 120 grams of 20 weight percent of chromic fluoride-on-carbon catalyst was packed in the downstream vertical piece of pipe and the empty upstream piece was employed as the preheater.

(a) Control Test

At atmospheric pressure and molten salt bath temperature of 375° C., a stream consisting of:
  HF (1.68 moles hr$^{-1}$); and
  1,1,2-trichloro-1,2,2-trifluoroethane (0.506 moles hr$^{-1}$)
was passed through the catalyst. Of the feed, 9.9 mole percent was found to have been converted to 1,2-dichloro-1,1,2,2-tetrafluoroethane at steady state.

(b) Activation

At atmospheric pressure and a molten salt bath temperature of 450° C., a stream consisting of:
  HCl (4.1×10$^{-3}$ moles hr$^{-1}$); and
  Cl$_2$ (8.2 to 12.3×10$^{-4}$ moles hr$^{-1}$, 20 to 30 mole percent)
was passed through the catalyst for 24 hours.

(c) Conversion Activity Test

Analysis of the effluent following activation showed that, under the conditions of the control test, 14.9 mole percent of the feed had been converted to 1,2-dichloro-1,1,2,2-tetrafluoroethane.

EXAMPLE 3

In a somewhat larger device than that earlier described, employing a 2 in. (5.1 cm) diameter 20 ft (6.1 M) long electrically heated reactor, a stream consisting of 23.6 moles hr$^{-1}$ of HCl was passed at 300 psig (21.1 kg cm$^{-2}$) through 9.1 kg of spent 20 weight percent CrF$_3$-on-carbon catalyst at 450° C. Thereafter, 3.8 moles hr$^{-1}$ of Cl$_2$ (13.9 mole percent) was admixed with the HCl stream and the mixture was fed for eight hours.

An accelerated life test of catalyst activity was carried out in the same equipment following an 8 hour treatment of the catalyst with HF at about 220° C. to 260° C. The accelerated life test was conducted at various peak temperatures between 327° C. to 372° C. over a period of 270 hours. One of the peak temperatures employed was 327° C. at which temperature a stream of 1,1,2-trichloro-1,2,2-trifluoroethane (22.0 moles hr$^{-1}$), 1,1,2,2-tetrachloro-1,2-difluoroethane (8.7 moles hr$^{-1}$), 10 moles of HCl hr$^{-1}$ as ballast simulating plant conditions, and HF (34.0 moles hr$^{-1}$), was converted to the extent of 8 mole percent to 1,1,2,2-tetrachloro-1,2-difluoroethane. Over the entire range of accelerated life test times and temperatures, the activated catalyst was found to produce conversions of about 18 to 290 times those observed with untreated catalyst under comparable conditions with substantially the same feed stream.

EXAMPLE 4

This Example was carried out in a commercial size upright cylindrical fixed bed catalytic reactor containing 82 parts by weight, per part of chlorine regenerant, of a spent 20 weight percent CrF$_3$-on-carbon catalyst. The device comprised ancillary equipment usual in the vapor phase production and separation of commercial perchlorofluoroethanes.

In the first step, the process charge was displaced from the reactor through the normal recovery train and the reactor was brought to 425° to 450° C. by passing through the reactor a preheated stream consisting of:

HCl (29 parts by weight hr$^{-1}$); and
Cl$_2$ (1 part by weight hr$^{-1}$, 1.7 mole percent)
at 290 psig (20.4 kg cm$^{-2}$).

The displacement of fluorine from the catalyst was regarded as complete when, after about 20 hours, the weight percent of HF in the effluent, consisting predominantly of HCl, had fallen to less than 0.3.

While maintaining the same pressure and flow through the reactor, the temperature was allowed to fall to 200° C. The composition of the inlet stream was then changed under the same pressure to:

HCl (13 parts by weight hr$^{-1}$); and
HF (13 parts by weight hr$^{-1}$).
The change was made gradually so as to control the exotherm of fluoride exchange and keep the peak temperature of the reactor at not more than about 400° C. The activation was complete when the exotherm front had passed through the reactor, which required about 10 hours.

The catalyst thus activated was found to initiate rapid halogen exchange at an inlet temperature of only 304° C.

The catalyst, activated in accordance with the procedure of this Example, displayed extremely good efficiency over a long period of time. For instance, during 67 days of continuous operation at about 310° C. inlet temperature, an inlet stream similar to that of Example 3 was converted to a composite stream consisting essentially of 6.1 mole percent, based on organics, of 1,2-dichloro-1,1,2,2-tetrafluoroethane in 1,1,2-trichloro-1,2,2-trifluoroethane. After this time period, the reaction temperature was increased gradually to maintain conversion rates. The overall productivity was found to be surprisingly good in terms of weight of product formed in the halogenexchange reaction per unit weight of catalyst before the catalyst became spent.

The embodiments of the invention in which an exclusive property or privilege is claimed are defined as follows:

1. A process for activating chromic fluoride halogen-exchange catalyst comprising the steps of:
   (i) contacting said catalyst with hydrogen chloride and then chlorine, in sequence, at a temperature sufficient to convert at least part of said chromic fluoride to chromic chloride, and
   (ii) contacting the chromic chloride-containing catalyst produced in step (i) with hydrogen fluoride to produce activated chromic fluoride catalyst.

2. A process for activating chromic fluoride halogen-exchange catalyst comprising the steps of
   (i) contacting said catalyst with hydrogen chloride and chlorine, simultaneously, at a temperature sufficient to convert at least part of said chromic fluoride to chromic chloride, and
   (ii) contacting the chromic chloride-containing catalyst produced in step (i) with hydrogen fluoride to produce activated chromic fluoride catalyst.

3. A process according to claim 1 or claim 2 comprising contacting the chromic chloride-containing catalyst of step (i) with hydrogen fluoride according to step (ii) while said catalyst is in use as a halogen-exchange catalyst.

4. A process according to claim 1 or claim 2 comprising contacting the chromic chloride-containing catalyst of step (i) with hydrogen fluoride according to step (ii) before said catalyst is placed in use as a halogen-exchange catalyst.

5. A process according to claim 1 or claim 2 comprising carrying out step (i) at a temperature between about 425° C. to 475° C.

6. A process according to claim 3 comprising carrying out step (i) at a temperature between about 425° to 475° C.

7. A process according to claim 4 comprising carrying out step (i) at a temperature between about 425° C. to 475° C.

8. A process according to claim 1 or claim 2 wherein the halogen-exchange catalyst is supported on a carbon support.

9. A process according to claim 1 or claim 2 comprising carrying out step (i) at a superatmospheric pressure.

10. A process according to claim 9 comprising employing a superatmospheric pressure between about 17 to 25 kilograms per square centimeter.

11. A process according to claim 7, wherein the catalyst is supported on a carbon support, comprising carrying out step (i) at a temperature between about 425° to 450° C. and a pressure of about 20 kilograms per square centimeter.

* * * * *